United States Patent
Schütz

(10) Patent No.: US 6,419,486 B1
(45) Date of Patent: Jul. 16, 2002

(54) FLUID RESERVOIR

(75) Inventor: Alfred Schütz, Zollikofen (CH)

(73) Assignee: Gimelli Produktions AG, Zollikofen (CH)

( * ) Notice: Subject to any disclaimer, the term of this patent is extended or adjusted under 35 U.S.C. 154(b) by 0 days.

(21) Appl. No.: 09/722,781

(22) Filed: Nov. 27, 2000

(51) Int. Cl.⁷ .............................................. A61C 17/00
(52) U.S. Cl. ....................................................... 433/80
(58) Field of Search ...................... 433/80, 28; 601/162, 601/163, 164

(56) References Cited

U.S. PATENT DOCUMENTS

| | | | |
|---|---|---|---|
| 4,302,186 A | 11/1981 | Cammack et al. ............ | 433/80 |
| 4,416,628 A | * 11/1983 | Cammack et al. ............ | 433/80 |
| 4,770,632 A | * 9/1988 | Ryder et al. ................... | 433/28 |
| 4,830,210 A | 5/1989 | Mabille ........................ | 215/309 |
| 5,060,825 A | 10/1991 | Palmer et al. ................. | 222/25 |

* cited by examiner

Primary Examiner—John J. Wilson
Assistant Examiner—Mellon Bumgarner
(74) Attorney, Agent, or Firm—Needle & Rosenberg, P.C.

(57) ABSTRACT

A fluid reservoir for an oral hygiene appliance has a floor valve in its floor which opens when the reservoir is placed on the oral hygiene appliance. The fluid reservoir is subdivided into two separate fluid chambers, each with a fluid outlet leading to the floor valve. The fluid outlets can be controlled by a manually operable selector valve in such a way that one fluid outlet is opened and the other is closed alternately.

29 Claims, 4 Drawing Sheets

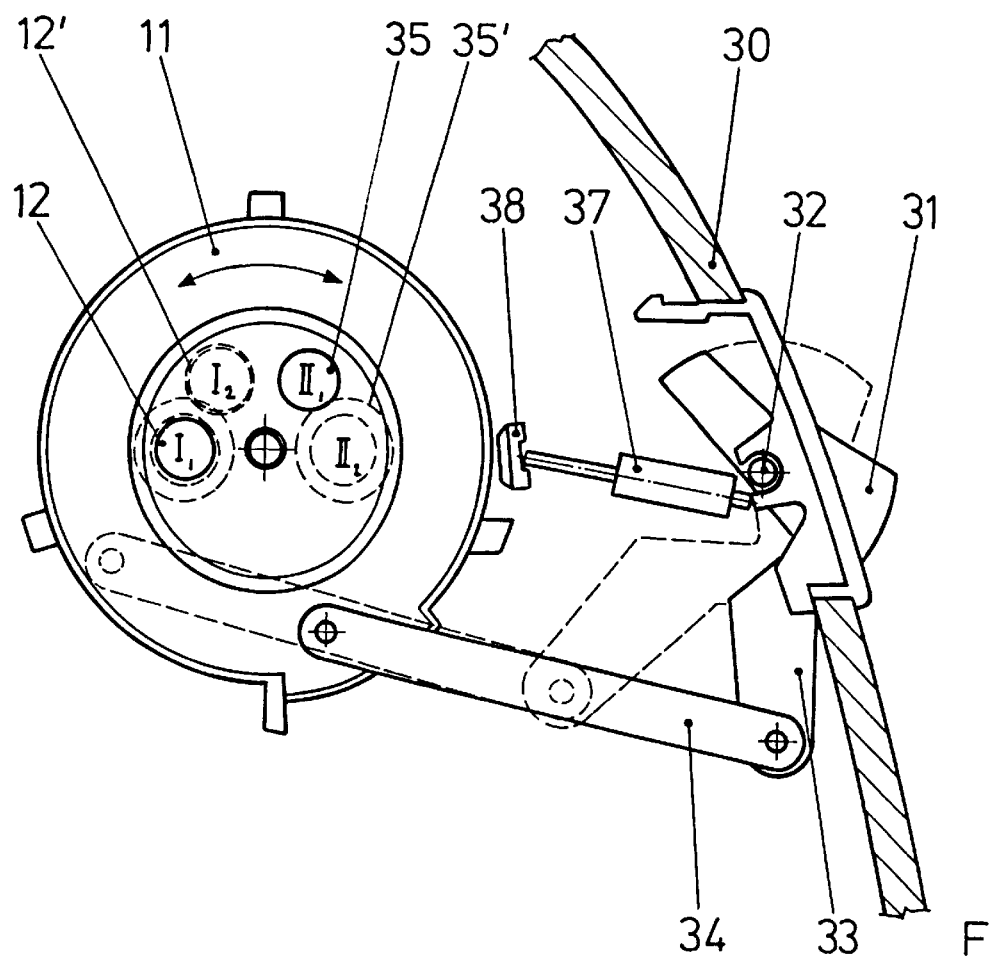
Fig. 6
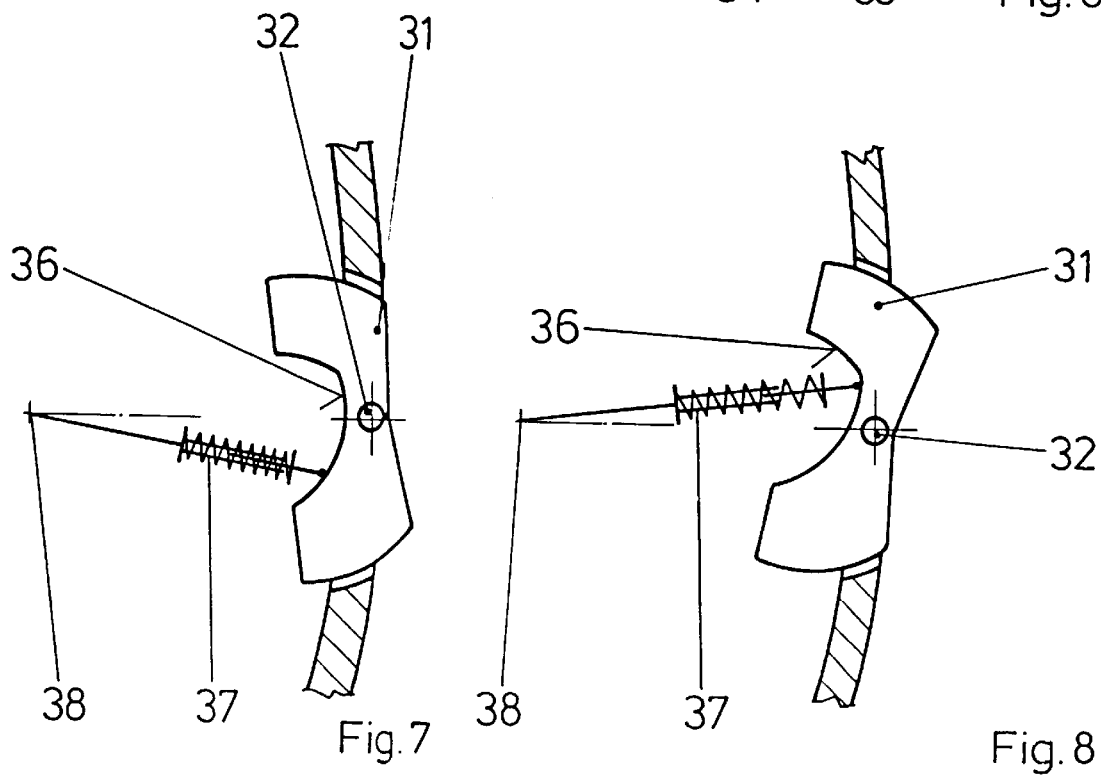
Fig. 7
Fig. 8

FLUID RESERVOIR

BACKGROUND OF THE INVENTION

1. Field of the Invention

The invention concerns a fluid reservoir for an oral hygiene appliance having a floor valve in its floor which opens when the reservoir is placed on the oral hygiene appliance.

2. Description of Related Art

A fluid reservoir of the preceding type is, for example, described in U.S. Pat. No. 4,302,186. The fluid reservoir can be filled with water separately from the oral hygiene appliance and be transported while full to the oral hygiene appliance, and automatically opens a connection to the oral hygiene appliance when it is set on the oral hygiene appliance.

SUMMARY OF THE INVENTION

One often has the desire to use a special mouthwash instead of clear water in the water reservoir of an oral hygiene appliance or to add mouthwash to the water in the reservoir. However, as the fluid reservoir has a relatively large volume, this leads to undesired high costs if one uses a mouthwash or water to which mouthwash has been added instead of clear water in the oral hygiene appliance from the beginning. Therefore, one often changes the fluid contained in the fluid reservoir shortly before finishing use of the oral hygiene appliance, which is, of course, inconvenient.

The invention has as its basis the problem of designing a fluid reservoir of the type initially mentioned in such a way that one can switch between at least two fluids in the easiest possible way.

This task is solved according to the invention in that the fluid reservoir has two separate fluid chambers, each having a fluid outlet, leading to the floor valve, connected to a manually operable selector valve which alternately opens one or the other fluid outlet.

Through this design of the fluid reservoir, one can connect the oral hygiene appliance during use to one or the other fluid chamber alternately. It thereby becomes possible, for example, to spray with a mouthwash only near the end of the cleaning process without having to change the fluid in the fluid reservoir in order to do so. Thanks to the invention, one can fill the two fluid chambers with the two fluids even before using the oral hygiene appliance. Furthermore, through the separate configuration of two fluid chambers, one can ensure that the reservoir is filled with only the small amount of the relatively expensive mouthwash actually needed for use at the end of the cleaning process.

The selector valve is particularly easy to operate and always opens either one or the other fluid outlet if, according to an advantageous development of the invention, the selector valve is preloaded by a bistable catch spring in its respective switch positions.

The fluid reservoir has a particularly simple structural design if the floor valve is positioned in a valve chamber provided under the floor of the fluid reservoir and if the selector valve is realized as a manually rotatable valve disk adjacent to the floor of the fluid reservoir between a closing element of the floor valve and the fluid outlet, having a channel which can alternately be brought into overlap with one or the other fluid outlet.

The means for operating the valve disk can be very simply designed if the valve disk is provided with a coaxial gearing and an axially displaceable rack is provided for rotating the valve disk.

The desired snapping function of the selector valve can be easily achieved if the rack is preloaded by the catch spring in two end positions.

The handling of the fluid reservoir is particularly simple if a two-arm rocking lever, movable around a swivel pin, is provided for actuating the rack which engages at one end with the rack and which has a pushbutton pressing against each of its lever arms. This embodiment makes it possible to operate the pushbutton with the same hand which carries the fluid reservoir while it is being carried, and thereby to open the desired fluid chamber.

When the selector valve is switched, it remains in the respective end position until the dead center position has been overcome if the rack is movably connected with the rocking lever of the to such a degree that, during switching from one to the other position, the rack is only pulled along after the dead center of position of the catch spring has been overcome. Through this design, the specific switch position of the selector valve is at first completely maintained. Only after overcoming the dead center position does the switching process of the selector valve begin, so it occurs very quickly and the selector valve is only in an intermediate position for a short time.

The desired play between the rack and the rocking lever can be realized in a simple way if the catch spring presses against a pin which is movably guided in a prong of a lever arm of the rocking lever on one side and supported on the other side in a recess of the rack, and if the pin can be moved against one of the two end surfaces of the recess at a time to displace the rack.

The operation of the valve disk is also possible through one rocker switch instead of two pushbuttons, if, according to another development of the invention, a connecting rod for rotating the valve disk is linked to the valve disk which is connected at its other end to a lever arm of a rocker switch.

In such an embodiment, the desired snapping function can be attained with simple means if the catch spring is realized as a telescopic rod and engages on a support of the fluid reservoir and a sliding surface of the rocker switch.

The invention allows various embodiments. Several of these are depicted in the drawings and will be described in the following. These show:

DETAILED DESCRIPTION OF THE PREFERRED EMBODIMENTS

Figure 1:
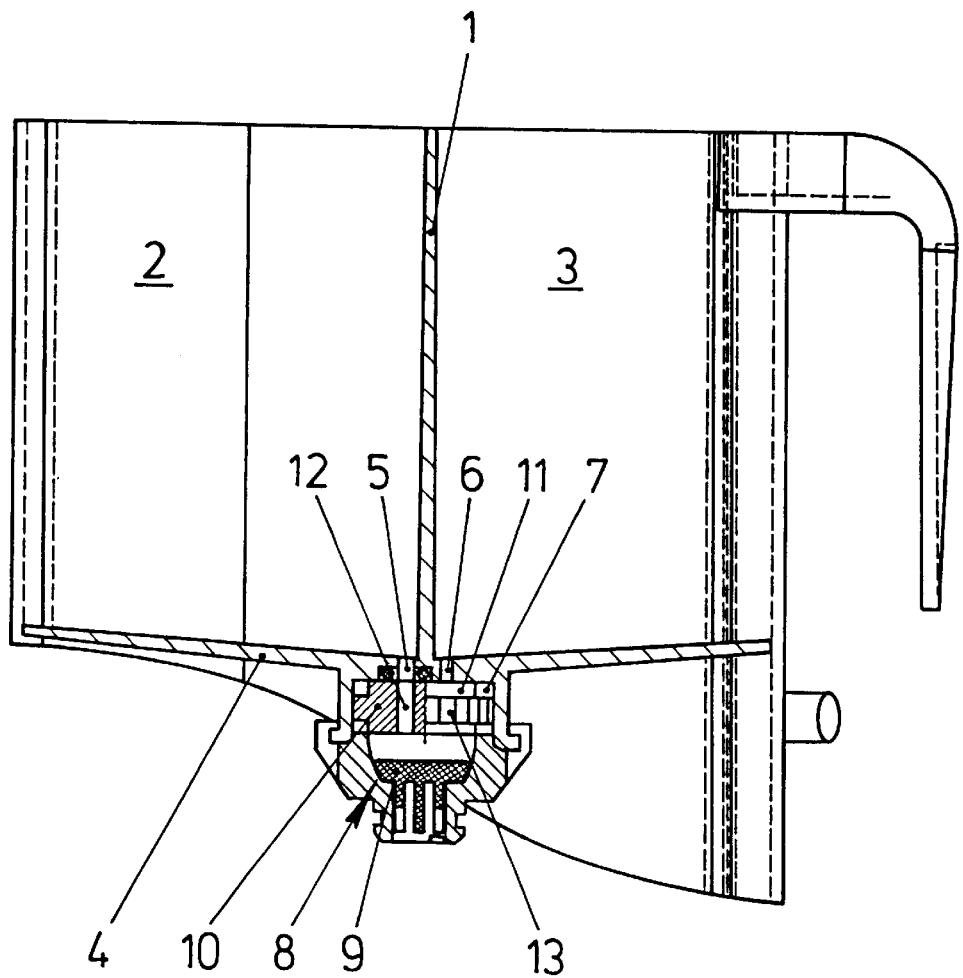
FIG. 1 a vertical section through a fluid reservoir according to the invention.

The fluid reservoir depicted in its entirety in FIG. 1 has a separating wall 1 which subdivides it into two fluid chambers 2, 3 separated from one another. These fluid chambers 2, 3 are delimited at the bottom by a floor 4 which sinks towards the middle of the fluid reservoir, and each has a fluid outlet 5, 6 immediately before the separating wall 1. The fluid outlets 5, 6 flow into a common valve chamber 7, molded onto the floor 4 of the fluid reservoir, in which a floor valve 8 is positioned. This valve has a closing element 9, which is pushed open in the usual way when the fluid reservoir is placed on an oral hygiene appliance. A selector valve 10 is positioned in the valve chamber 7 above the floor valve 8 which makes it possible to alternately connect one of the fluid outlets 5, 6 with the valve chamber 7 and to thereby close the other fluid outlet 5, 6.

For this purpose, the selector valve 10 has a valve disk 11, rotatably positioned in the valve chamber 7, which has a channel 12 which can alternately be brought into overlap with either one fluid outlet 5 or the other fluid outlet 6. The valve disk 11 is provided with a coaxial gearing 13 for its operation.

Figure 2:
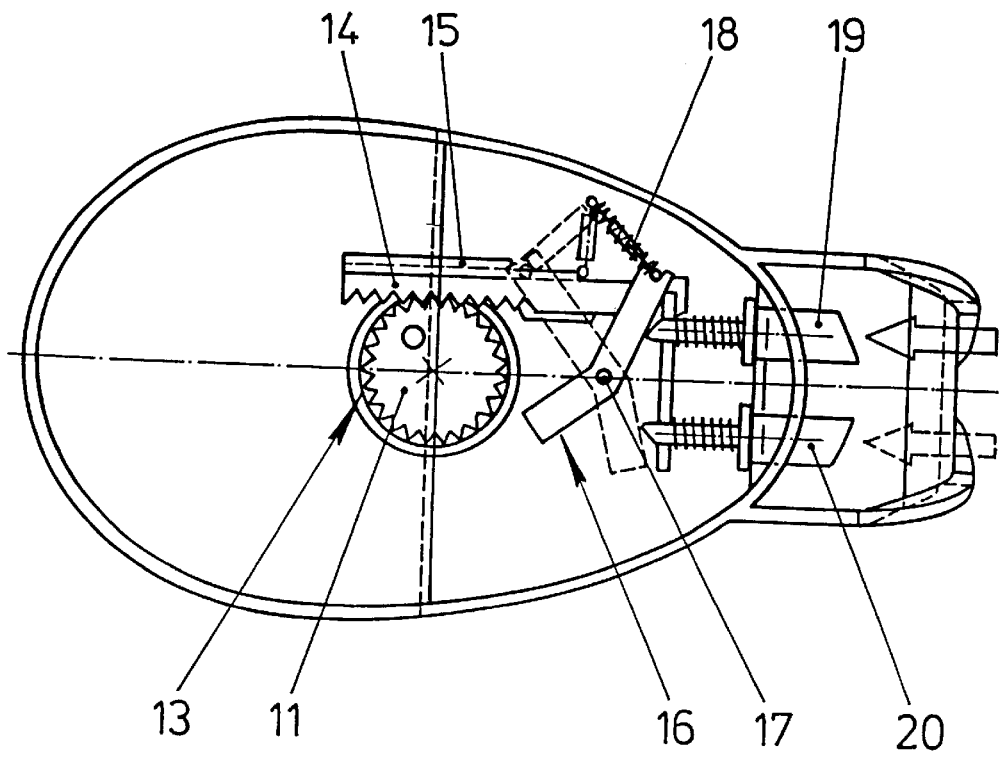
FIG. 2 a horizontal section through the fluid reservoir.

FIG. 2 illustrates that a rack 14 engages in the gearing 13 in order to rotate the valve disk 11. A rocking lever 16, which can be swiveled around a swivel pin 17, serves to displace the rack 14 in a slide guide 15. A catch spring 18 preloads the rocking lever 16 or the rack 14 in the position depicted. If the pushbutton 19 is pressed, then the rocking lever 16 swivels counterclockwise. The catch spring 18 is first compressed, overcomes a dead center in the middle position, and then snaps the rocking lever 16 into the dashed position, whereby the rack 14 is thereby correspondingly displaced to the right and the valve disk 11 rotates. If one then wishes to switch back to the old position, one presses a pushbutton 20, which affects the other lever arm of the rocking lever 16 than the pushbutton 19, whereby one then swivels the rocking lever 16 clockwise and it reaches its end position on its own after the dead center of the catch spring 18 has been overcome.

Figure 3:
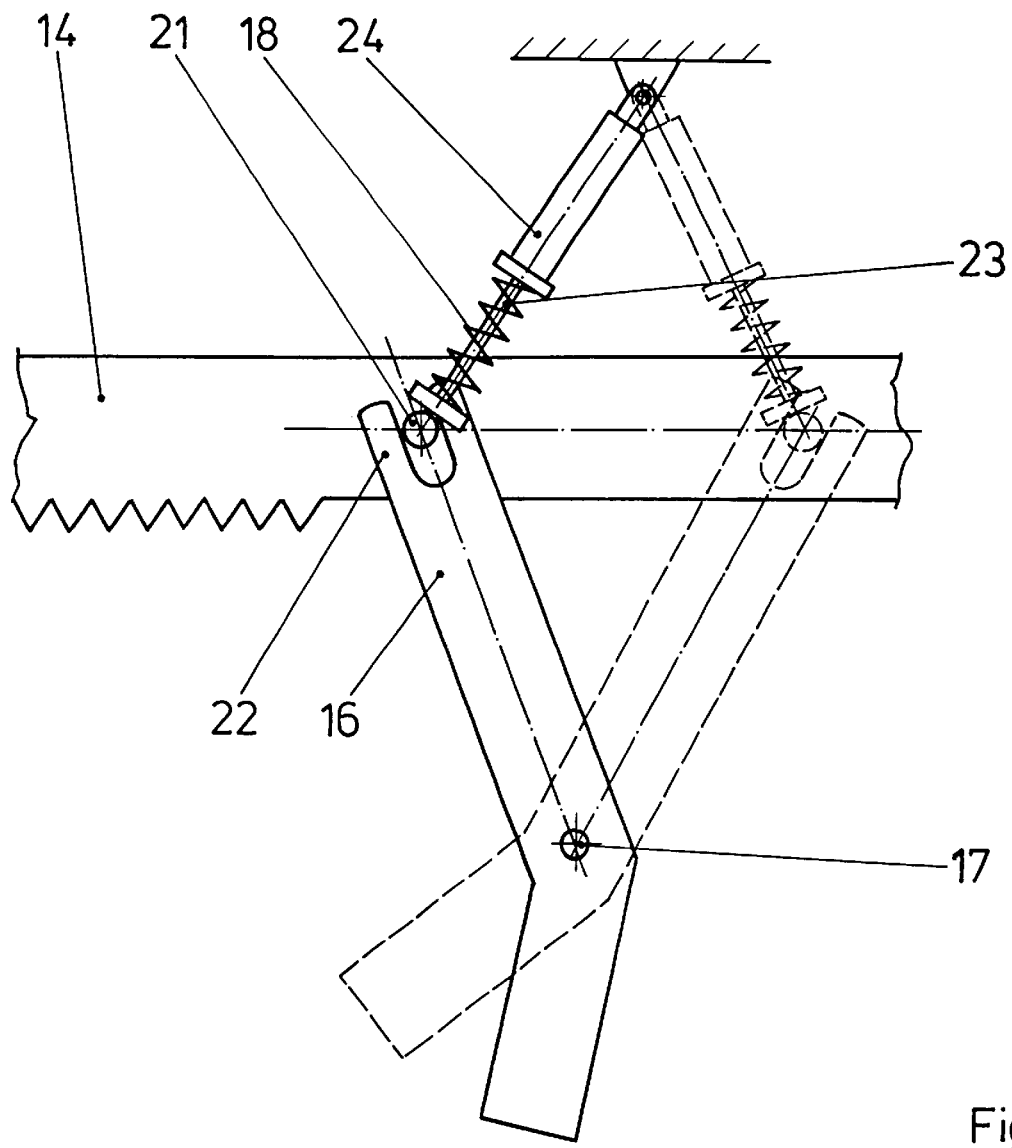
FIG. 3 a schematic diagram of the operation of a selector valve of the fluid reservoir, FIG. 4 an enlarged-scale sectional depiction of the region of the selector valve of the fluid reservoir, FIG. 5 a schematic diagram of a second embodiment of the operation of the selector valve, FIG. 6 a horizontal section through the fluid reservoir with an altered operation of the selector valve, FIG. 7 a rocker switch of the fluid reservoir in a first switch position, FIG. 8 the rocker switch according to FIG. 7 in a second switch position.

The origin of the snapping effect can be most quickly understood from FIG. 3. A pin 21, for example, is attached to the rack 14, via which a prong 22 of the rocking lever 16 engages. The catch spring 18 presses against this pin 21 with a piston rod 23 attached to the pin 21. If one moves the rack 14 to the right, then the piston rod 23 is pushed, against the action of the catch spring 18, into a cylinder 24 and, due to the spring tension, travels back out of this cylinder 24 as soon as a dead center has been overcome.

Figure 4:
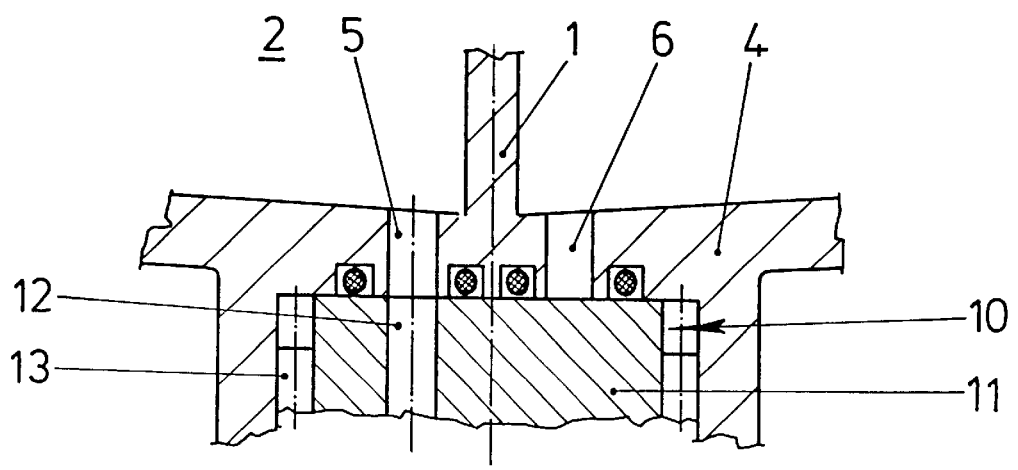

FIG. 4 serves to further illustrate the design of the selector valve 10. It can be seen that its valve disk 11 presses from below against the floor 4 of the water reservoir, forming a seal. Its channel 12 is aligned with the fluid outlet 5, so that fluid can run out of the fluid chamber 2. The fluid outlet 6 is simultaneously closed by the valve disk 11.

Figure 5:
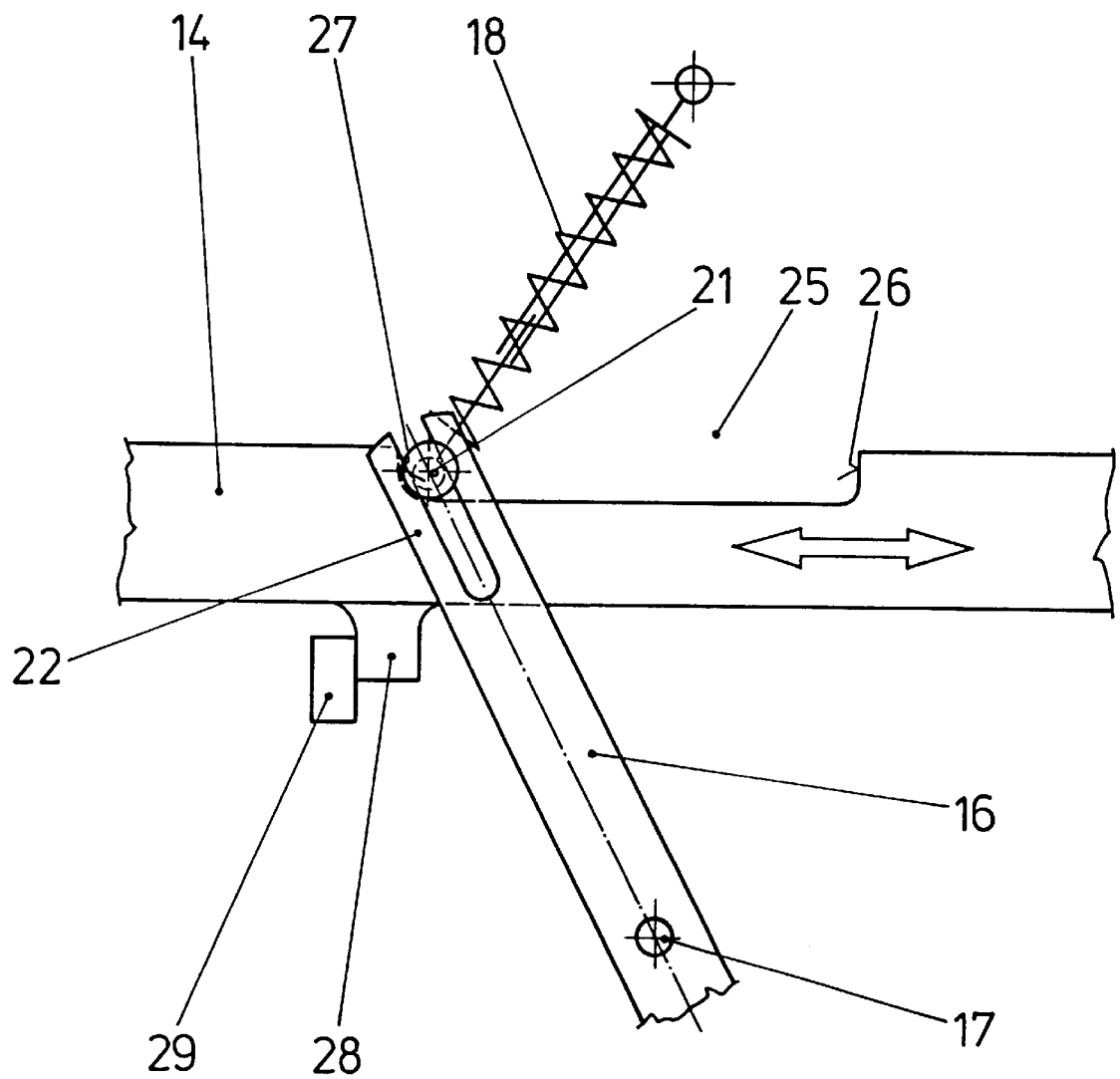

In the embodiment according to FIG. 5, the rack 14 has a recess 25 delimited by two end surfaces 26, 27. In the position of the catch spring 18 indicated, the pin 21 presses against the left end surface 27, so that the rack 14 is preloaded to the left and presses with a stop cam 28 against a stop 29. If one swivels the rocking lever 16 clockwise around its swivel pin 17, then it moves the pin 27 with its prong 22 to the right until the dead center position of the catch spring 18 has been overcome. The catch spring 18 then moves the pin 27 against the right end surface 26 and consequently moves the rack 14 to the right until it reaches a right stop (not shown).

FIG. 6 partially shows a housing 30 of the fluid reservoir in which a rocker switch 31 is positioned so it swivels around an axle 32. The rocker switch 31 has a rigidly attached lever arm 33 inside the housing 30 to which a connecting rod 34 is linked This connecting rod 34 is articulated at its other end with the valve disk 11. This valve disk 11 has two channels 12 and 35 in this embodiment. In the position depicted, the channel 12, for example, is in such a position that fluid is able to flow out of a fluid chamber 2, while the other channel 35 is not aligned with the fluid outlet 6 of the other fluid chamber 3 shown in the present figure, and this outlet is therefore blocked. If the valve disk 11 is rotated clockwise, then the channel 35 reaches a position aligned with the fluid outlet 6, so that the fluid chamber 3 is able to flow while the fluid chamber 2 is blocked.

The rotational movement of the valve disk 11 occurs when one swivels the rocker switch 31 clockwise around the axle 32. The connecting rod 34 seen in FIG. 6 thereby moves left and rotates the valve disk 11. The position of the valve disk 11 should, again, be bistable. Therefore, the rocker switch 31 is designed to be bistable in this embodiment, which is illustrated in FIGS. 7 and 8.

As can be seen in FIGS. 7 and 8, the rocker switch 31 has a sliding surface 36 against which a telescopic rod 37 is supported with preloading. The telescopic rod 37 is swivel-mounted at its other end in a support 38. Its preloads the rocker switch 31 in the position shown in FIG. 7. If one presses on the lower region of the rocker switch 31 shown in FIG. 7 and swivels it around the axle 32, the telescopic rod 37 first slips across the sliding surface 36 into a middle, labile position and then snaps into the opposite position shown in FIG. 8, so that the rocker switch 31 snaps itself into its second switch position.

LIST OF REFERENCE NUMBERS

1 Separating wall
2 Fluid chamber
3 Fluid chamber
4 Floor
5 Fluid outlet
6 Fluid outlet
7 Valve chamber
8 Floor valve
9 Closing element
10 Selector valve
11 Valve disk
12 Channel
13 Gearing
14 Rack
15 Slide guide
16 Rocking lever
17 Swivel pin
18 Catch spring
19 Pushbutton
20 Pushbutton
21 Pin
22 Prong
23 Piston rod
24 Cylinder
25 Recess
26 End surface
27 End surface
28 Stop cam
29 Stop
30 Housing
31 Rocker switch
32 Axle
33 Lever arm
34 Connecting rod
35 Channel 36 Sliding surface
37 Telescopic rod
38 Support

What is claimed:

1. Fluid reservoir for an oral hygiene appliance, the fluid reservoir comprising a floor which has a floor valve that opens when the reservoir is placed on the oral hygiene appliance, characterized in that the fluid reservoir has two separate fluid chambers, each with a fluid outlet, leading to the floor valve that is connected to a manually operable selector valve which can alternately open one or the other fluid outlet.

2. Fluid reservoir according to claim 1, characterized in that the selector valve is preloaded by a bistable catch spring into a respective switch position.

3. Fluid reservoir according to claim 2, characterized in that the selector valve is positioned in a valve chamber provided below the floor of the fluid reservoir and the selector valve is realized as a manually rotatable valve disk, adjacent to the floor of the fluid reservoir between a closing element of the floor valve and the fluid outlets, having a channel which can alternately be operably engaged with one or the other fluid outlet.

4. Fluid reservoir according to claim 3, further comprising an axially movable rack, characterized in that for operation of the rack, a two-arm rocking lever movable around a swivel pin is provided which engages at one end with the rack and whose lever arms each have a pushbutton pressing against them.

5. Fluid reservoir according to claim 4, characterized in that a connecting rod, which is connected on the other end to a lever arm of a rocker switch, is linked to the valve disk for rotation of the valve disk.

6. Fluid reservoir according to claim 3, characterized in that a connecting rod, which is connected on the other end to a lever arm of a rocker switch, is linked to the valve disk for rotation of the valve disk.

7. Fluid reservoir according to claim 2, further comprising an axially movable rack, characterized in that for operation of the rack, a two-arm rocking lever movable around a swivel pin is provided which engages at one end with the rack and whose lever arms each have a pushbutton pressing against them.

8. Fluid reservoir according to claim 7, further comprising a manually rotatable valve disk, characterized in that a connecting rod, which is connected on the other end to a lever arm of a rocker switch, is linked to the valve disk for rotation of the valve disk.

9. Fluid reservoir according to claim 2, further comprising a manually rotatable valve disk, characterized in that a connecting rod, which is connected on the other end to a lever arm of a rocker switch, is linked to the valve disk for rotation of the valve disk.

10. Fluid reservoir according to claim 1, characterized in that the selector valve is positioned in a valve chamber provided below the floor of the fluid reservoir and the selector valve is realized as a manually rotatable valve disk, adjacent to the floor of the fluid reservoir between a closing element of the floor valve and the fluid outlets, having a channel which can alternately be operably engaged with one or the other fluid outlet.

11. Fluid reservoir according to claim 10, characterized in that the valve disk is provided with a coaxial gearing and an axially movable rack is provided for rotation of the valve disk.

12. Fluid reservoir according to claim 11, characterized in that the rack is preloaded into two end positions by a catch spring.

13. Fluid reservoir according to claim 12, characterized in that, for operation of the rack, a two-arm rocking lever movable around a swivel pin is provided which engages at one end with the rack and whose lever arms each have a pushbutton pressing against them.

14. Fluid reservoir according to claim 13, characterized in that a connecting rod, which is connected on the other end to a lever arm of a rocker switch, is linked to the valve disk for rotation of the valve disk.

15. Fluid reservoir according to claim 12, characterized in that a connecting rod, which is connected on the other end to a lever arm of a rocker switch, is linked to the valve disk for rotation of the valve disk.

16. Fluid reservoir according to claim 11, characterized in that, for operation of the rack, a two-arm rocking lever movable around a swivel pin is provided which engages at one end with the rack and whose lever arms each have a pushbutton pressing against them.

17. Fluid reservoir according to claim 16, characterized in that a connecting rod, which is connected on the other end to a lever arm of a rocker switch, is linked to the valve disk for rotation of the valve disk.

18. Fluid reservoir according to claim 11, characterized in that a connecting rod, which is connected on the other end to a lever arm of a rocker switch, is linked to the valve disk for rotation of the valve disk.

19. Fluid reservoir according to claim 10, further comprising an axially movable rack, characterized in that for operation of the rack, a two-arm rocking lever movable around a swivel pin is provided which engages at one end with the rack and whose lever arms each have a pushbutton pressing against them.

20. Fluid reservoir according to claim 19, characterized in that a connecting rod, which is connected on the other end to a lever arm of a rocker switch, is linked to the valve disk for rotation of the valve disk.

21. Fluid reservoir according to claim 10, characterized in that a connecting rod, which is connected on the other end to a lever arm of a rocker switch, is linked to the valve disk for rotation of the valve disk.

22. Fluid reservoir according to claim 1, further comprising an axially movable rack, characterized in that for operation of the rack, a two-arm rocking lever movable around a swivel pin is provided which engages at one end with the rack and whose lever arms each have a pushbutton pressing against them.

23. Fluid reservoir according to claim 22, further comprising a catch spring, characterized in that the rack is movably coupled with the rocking lever to such a degree that, during switching from one to the other position, the rack is pulled along only after the dead center position of the catch spring has been overcome.

24. Fluid reservoir according to claim 23, characterized in that the catch spring supports itself on a pin which is movably guided on one side in a prong of a lever arm of the rocking lever and is supported on the other side in a recess of the rack, and the pin is movable against one of two end surfaces of the recess at a time for displacement of the rack.

25. Fluid reservoir according to claim 24, further comprising a manually rotatable valve disk, characterized in that a connecting rod which is connected on the other end to a lever arm of a rocker switch is linked to the valve disk for rotation of the valve disk.

26. Fluid reservoir according to claim 23, further comprising a manually rotatable valve disk, characterized in that a connecting rod which is connected on the other end to a lever arm of a rocker switch, is linked to the valve disk for rotation of the valve disk.

27. Fluid reservoir according to claim 22, further comprising a manually rotatable valve disk, characterized in that a connecting rod, which is connected on the other end to a lever arm of a rocker switch, is linked to the valve disk for rotation of the valve disk.

28. Fluid reservoir according to claim 1, further comprising a manually rotatable valve disk, characterized in that a connecting rod, which is connected on the other end to a lever arm of a rocker switch, is linked to the valve disk for rotation of the valve disk.

29. Fluid reservoir according to claim 28, further comprising a catch spring, characterized in that the catch spring is realized as a telescopic rod and engages on a support of the fluid reservoir and a sliding surface of the rocker switch.

* * * * *

UNITED STATES PATENT AND TRADEMARK OFFICE
CERTIFICATE OF CORRECTION

PATENT NO. : 6,419,486 B1
DATED : July 16, 2002
INVENTOR(S) : Schütz

It is certified that error appears in the above-identified patent and that said Letters Patent is hereby corrected as shown below:

Title page,
After Item [21], insert -- [30] Foreign Application Priority Data,
  December 3, 1999   (DE)……………...299 21 192.4
  February 2, 2000   (DE)……………...100 04 535.9 --

Signed and Sealed this

Thirteenth Day of July, 2004

JON W. DUDAS
*Acting Director of the United States Patent and Trademark Office*